United States Patent [19]

Sinnokrot

[11] Patent Number: 4,790,180
[45] Date of Patent: Dec. 13, 1988

[54] METHOD FOR DETERMINING FLUID CHARACTERISTICS OF SUBTERRANEAN FORMATIONS

[75] Inventor: Ali A. Sinnokrot, Dallas, Tex.

[73] Assignee: Mobil Oil Corporation, New York, N.Y.

[21] Appl. No.: 156,069

[22] Filed: Feb. 16, 1988

[51] Int. Cl.$^4$ ............................................. E21B 49/02
[52] U.S. Cl. ................................................... 73/153
[58] Field of Search ......................... 73/38, 153, 152; 166/250

[56] References Cited

U.S. PATENT DOCUMENTS

| | | | |
|---|---|---|---|
| 3,839,899 | 10/1974 | McMillen | 73/38 |
| 4,005,290 | 1/1977 | Allen | 250/266 |
| 4,021,666 | 5/1977 | Allen | 250/265 |
| 4,413,512 | 11/1983 | Zemanek, Jr. | 73/152 |
| 4,506,548 | 3/1985 | Zemanek, Jr. | 73/152 |
| 4,508,169 | 4/1985 | Mut et al. | 166/250 |
| 4,517,836 | 5/1985 | Lyle, Jr. et al. | 73/152 |
| 4,649,483 | 3/1987 | Dixon, Jr. | 364/422 |
| 4,687,523 | 8/1987 | Hall et al. | 134/30 |
| 4,688,238 | 8/1987 | Sprunt et al. | 378/4 |

OTHER PUBLICATIONS

"Petroleum Production Engineering", L. C. Uren, McGraw-Hill Book Co., Inc., 4th Ed., pp. 660–669.
"API Recommended Practice for Core-Analysis Procedure", Am. Petroleum Institute, New York, N.Y., 1st Ed., Aug. 1960, pp. 2–55.

Primary Examiner—Stewart J. Levy
Assistant Examiner—Kevin D. O'Shea
Attorney, Agent, or Firm—Alexander J. McKillop; Michael G. Gilman; George W. Hager, Jr.

[57] ABSTRACT

Core samples are obtained from a plurality of differing depths in a subterranean formation. The samples are dried to effect an evaporation of the water content, leaving behind a salt precipitate. The dried samples are weighed. The salt precipitate is then leached out of the samples and the samples are again weighed, the difference in such weighings identifying the amount of salt precipitate. Alternatively, the salt content can be more accurately determined by chemical analysis of the leached solution. A measurement is made of the pore volume of the samples. From the measured weights of salt precipitates and sample pore volumes, the salt content in mass per unit volume is determined for each sample. Such salt content is plotted versus formation depth from which the core samples were taken. Trends in such plotted salt content are used to identify fluid characteristics of the formations at the in-situ reservoir conditions of pressure and temperature and at the in-situ wettability state of the reservoir.

11 Claims, 4 Drawing Sheets

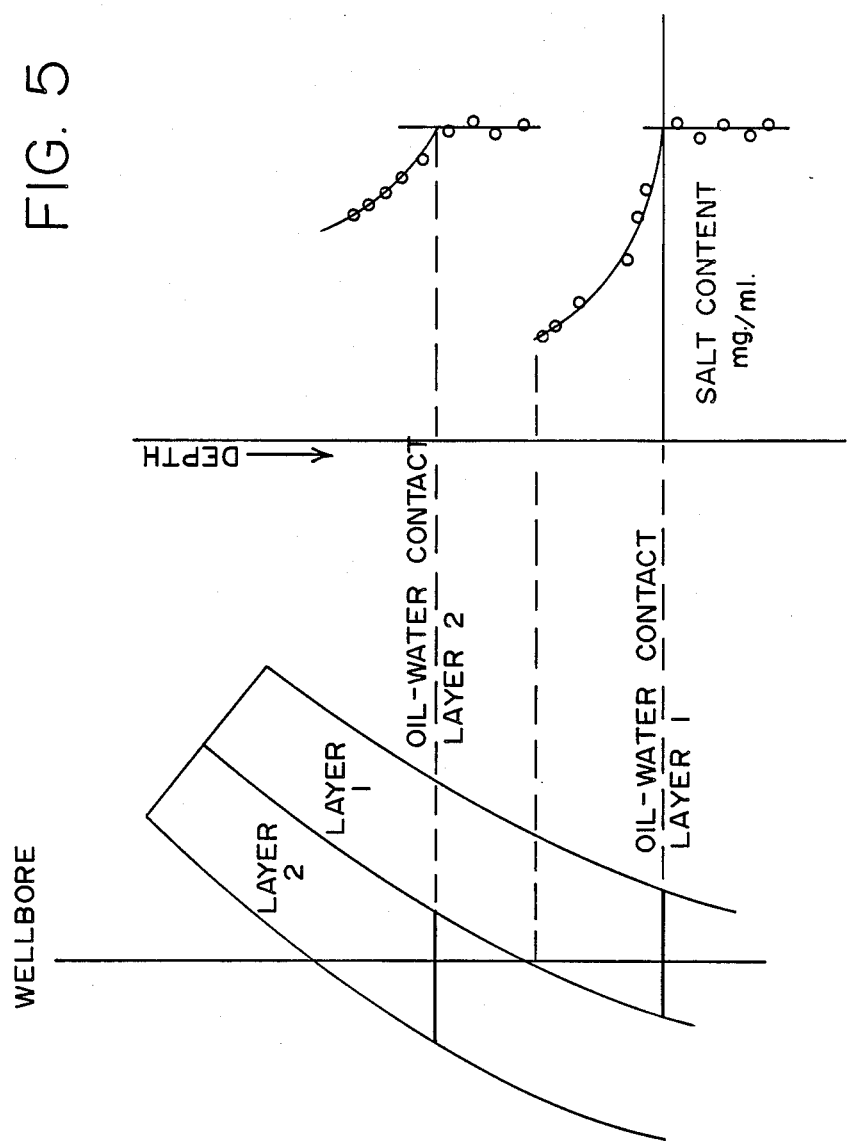

METHOD FOR DETERMINING FLUID CHARACTERISTICS OF SUBTERRANEAN FORMATIONS

BACKGROUND OF THE INVENTION

This invention relates to the area of oil and natural gas exploration and, more particularly, to a method for identifying regions of rock formations having significant water saturations from which hydrocarbons may be produced without significant attendant water production.

Subsurface reservoirs of natural gas and petroleum, hereinafter referred to generically as "hydrocarbons" are typically found trapped in permeable geological strata beneath a layer of impermeable strata material. A hydrocarbon will "float" upon any ground water present although typically, a transition zone will exist between the two fluids due to the water being raised by capillary action of the permeable strata material. In some regions, impermeable layers may be relatively closely stacked atop one another trapping thin zones of what may be essentially hydrocarbons, essentially water or mixed hydrocarbons and water. A well bore dropped through the formation and various layers may produce water if tapped (completed) in a transition region or mixed hydrocarbon and water zone. The determination of water saturation aids in the selection of completion intervals and in estimating the amount of hydrocarbons in place. Errors in water saturation determinations can result in (a) erroneous estimates of hydrocarbons in place, (b) the tapping of intervals with excessive amount of attendant water production, originally believed they would be predominantly productive of hydrocarbons, resulting in increased costs of production, and (c) the bypassing of intervals originally believed they would produce an excessive amount of attendant water.

Water saturation present at various levels of a formation is typically determined from interpretation of conventional electrical (i.e., resistivity) logs taken through a borehole dropped through the formation. Water saturation of the available pore space of the formation is determined from the resistivity log measurements using the Archie equation:

$$S_w{}^n = aR_w/\phi^m R_t, \tag{1}$$

where "$S_w$" is the fractional water saturation (i.e. free and bound water of the formation expressed as a percent of the available pore space of the formation), "a" is a formation resistivity coefficient, "$R_w$" is the formation water resistivity, "$\phi$" is the formation porosity, "$R_t$" is the formation resistivity indicated by the resistivity log, "n" is the saturation exponent and "m" is the porosity or cementation exponent. The Archie equation may be expressed in other ways and there are numerous methods in the art for determining, measuring or otherwise obtaining the various components needed to predict fractional water saturation $S_w$ from the log-indicated resistivity, $R_t$, using the equation in any of its forms.

The desired oil saturation estimate $S_o$ can be determined in accordance with the following expression after solving eq. (1) for water saturation $S_w$:

$$S_o = 1 - S_w \tag{2}$$

In gas reservoirs, the gas saturation, Sg, is:

$$Sg = 1 - Sw \tag{3}$$

While such a resistivity log interpretation is used to determine water saturation, it can be adversely affected by various factors such as lithologic changes and mineral composition, hole size, bed thickness, type of mud and filtrate invasion. Also, measurement of the saturation exponent "n" for use in solving the Archie equation for water saturation may be unreliable.

Other available methods for water saturation determination include well tests and core analysis. Drill stem tests provide data on the type and amounts of fluids produced from selected intervals. They do not provide fluid saturation data and cannot be used to define fluid-water contacts. The produced water could be due to water coning from a lower interval, or water intrusion from an upper interval through leaky casing or faulty cement job. Repeat formation testers do not provide fluid saturation data, but can furnish reliable fluid-water contact estimates under favorable conditions. Tool problems such as differential sticking, seal failure and probe plugging, or supercharging and threshold phenomena can limit their applicability. Laboratory analysis on core samples cut with an oil base mud can provide a qualitative indication of water saturation above the transition zone. Water loss due to evaporation during core handling operations can be excessive, especially if the reservoir temperature is relatively high. Such analysis fails to identify the oil-water contact in oil reservoirs because the filtrate can indicate oil saturation below the free water level. It is also not applicable in gas wells, especially if the bottom hole temperature is higher than the boiling point of water. Excessive core water evaporation at the surface can mask the actual increase in its saturation with depth, thus rendering the technique useless. Laboratory capillary pressure tests provide data relating the capillary pressure to water saturation above the free water level. In applying the data to an actual reservoir, the free water level must be determined by other means. The capillary pressure across an interface of a pair of fluids, such as oil and water, is defined as:

$$Pc = Po - Pw = \frac{2\delta_{ow} \cos\theta}{r} \tag{4}$$

where "Po" is the oil phase pressure, "Pw" is the water phase pressure, "$\delta_{ow}$" is the interfacial tension between the oil and water, "$\phi$" is the contact angle of the denser phase with the solid surface, and "r" is the radius of the capillary opening. The balance between capillary and gravitational forces yields:

$$Pc = \Delta\rho g h \tag{5}$$

where "$\Delta\rho$" is the density difference between water and oil, "g" is the acceleration due to gravity, and "h" is the height above the oil-water contact. Capillary pressure data obtained at laboratory conditions using laboratory fluids must be converted to reservoir conditions using the following relationship:

$$Pc_R = Pc_L \frac{(\delta_{ow}\cos\theta)_R}{(\delta_{ow}\cos\theta)_L} \tag{6}$$

where the subscripts "R" and "L" denote reservoir and laboratory conditions, respectively. The ratio of interfacial tensions in Equation (6) is difficult to measure while the contact angles are usually obtained using polished crystals of silica or limestone. Consequently, the data conversion using Equation (6) may not be adequate. In addition, core sample wettability may be different from in-situ reservoir wettability, thus resulting in non-representative data.

It is therefore a specific object of the present invention to provide a new method for determining subterranean formation fluid characteristics which overcomes the problems and limitations of the foregoing described prior art methods.

SUMMARY OF THE INVENTION

The present invention is directed to a method for determining fluid characteristics of subterranean formations. More particularly, core samples are obtained from a plurality of differing formation depths. The samples are dried to effect an evaporation of the water content, leaving behind a salt precipitate. The salt content in mass per unit pore volume is determined for each sample. The salt content is then correlated for the plurality of core samples, such as by plotting salt content versus formation depth from which the samples were obtained. Trends in such correlated salt contents are used to identify various formation fluid characteristics.

In one aspect, the salt content is determined in accordance with the following method. The dried samples are weighed. The salt precipitate is then leached out of the samples and the samples are again weighed, the difference in such weighings identifying the amount of salt precipitate. A measurement is made of the pore volume of the samples. Salt content is determined from the measured weights of salt precipitate and core sample pore volumes.

In another method, salt is leached from the core samples and salt content is determined by chemical compositional and volume analysis of the leached solution when the salinity of the water or the amount of precipitated salt is too low for an accurate salt content determination by the weight difference method.

In a further aspect, the salt content correlation with depth identifies the saturation profile of the subterranean formation. In a more specific aspect, a 100% fluid saturation is determined for a formation interval over which there is no identifiable change in salt content with depth. The top of the 100% fluid saturated interval may be identified on a water table or, in the alternative, as a hydrocarbon-water interface. Also the effect of formation layering or permeability variation can be identified. In another aspect, the information as to salt content can be used in converting laboratory derived capillary pressure data to reservoir conditions. The saturation data, so derived, can be used to calibrate electric logs in uncored wells in the same reservoir to yield additional fluid saturation data.

BRIEF DESCRIPTION OF THE DRAWINGS

FIG. 5 depicts the behavior of salt content data with depth for a layered reservoir.

DESCRIPTION OF THE PREFERRED EMBODIMENT

Figure 1:
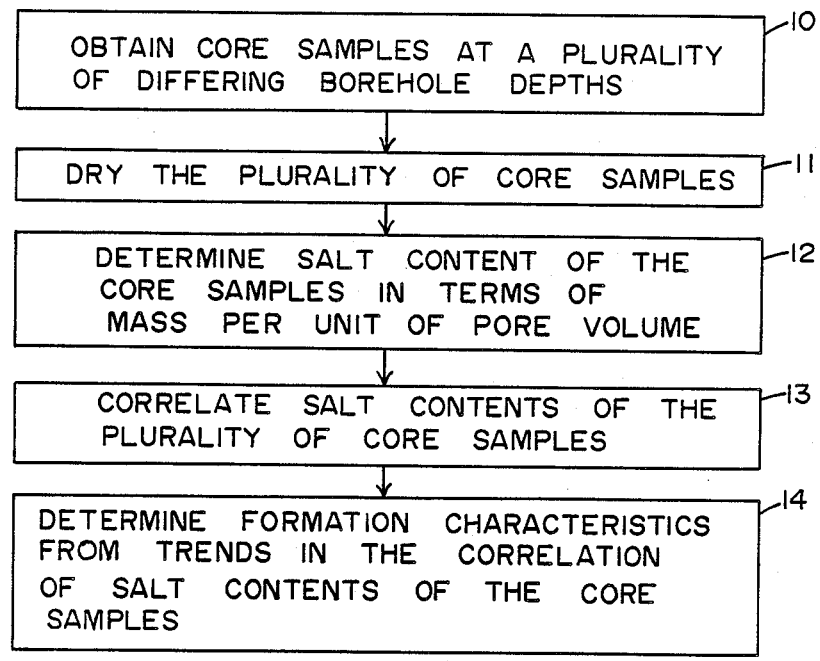
FIGS. 1–3 are flow charts depicting the steps carried out in accordance with the method of the present invention in identifying salt content of core samples from subterranean formations for use in identifying formation characteristics.

The method of the present invention may best be understood by the following descriptions taken in conjunction with the flow chart of FIG. 1. Initially at step 10, core samples are obtained at a plurality of differing depths from a subterranean formation during drilling for petroleum exploration and production. These core samples are then to be analyzed for salt content in accordance with the present invention to determine fluid saturation in oil and gas reservoirs and to determine hydrocarbon-water contact. As water saturation increases with depth, so does salt content. If overbalance conditions and filtrate loss are kept to a minimum, the salt content will be a function of water saturation. It will achieve constancy below the 100% water level.

Preferably the whole core samples are frozen at the rig site and kept frozen until the start of analysis. Freezing prevents mixing of mud filtrate with formation water and suppresses ionic diffusion. It is recommended even if the coring fluid is oil-base to guard against mud breakdown that may cause the filtrate to be water instead of oil. Concentric, vertical core plugs are cut at selected depths using liquid nitrogen as bit coolant. The size of the plugs will vary depending upon the degree of mud filtrate invasion, rock porosity, salinity of the water and method of analysis for salt content. Filtrate invasion can be estimated by tagging the coring fluid with a suitable tracer such as tritium or fluorescein dye and analyzing for the tracer concentration at various distances from the center of the core. If invasion is low, a two-inch diameter by two-inch long plug is adequate for rocks with average porosity of 15% and water salinity in excess of 100,000 parts per million. The diameter and length of the plugs may vary to suit particular conditions. At Step 11, the plugs are introduced into a conventional, controlled-temperature vacuum oven utilizing a temperature of about 85° C. The plugs are dried until all the water content has evaporated, leaving behind its salt precipitate. This may be indicated when there is not further weight change with continued drying. Following drying, the plugs may be cooled in a conventional desiccator.

Figure 2:
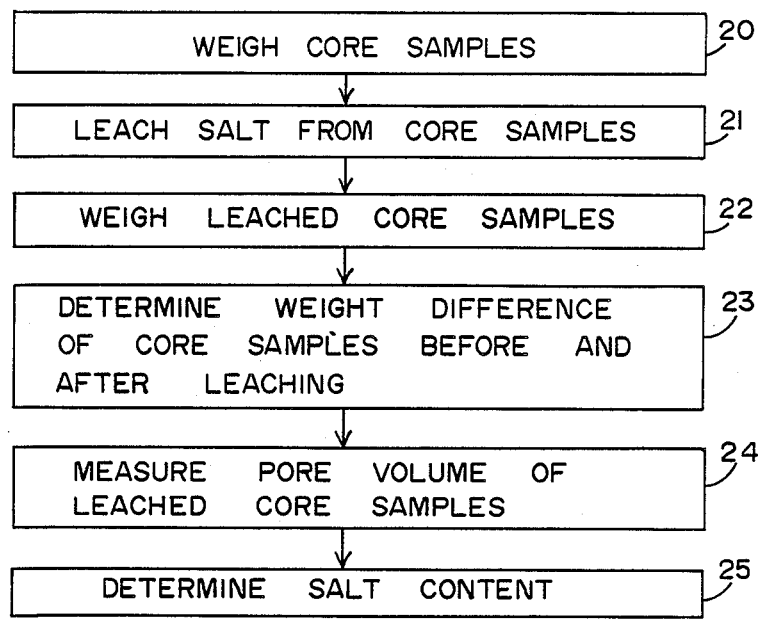

It is then necessary to determine the salt content (i.e., precipitate) in each core plug at step 12. In one method, as shown in FIG. 2, the plugs are weighed at step 20 and then the salt is leached from the plugs at step 21 with any of a plurality of acceptable solvents which will not attack, alter or destroy the structure of the core plugs. Distilled water can be used as a solvent in carbonate and sandstone rocks that do not contain hydratable clays. Where clays are present, methyl alcohol can be used. Following such leaching, the plugs are again dried at about 85° C. in a vacuum oven, cooled in a desiccator and weighed at step 22. The weight difference for each plug as obtained in step 23 represents the salt mass of such plug. When core plugs contain oil or gas condensate, the weighing step would consist of oil extraction from the plugs using a suitable solvent such as toluene. Conventional methods for drying and oil extraction are described in *API Recommended Practice For Core-Analysis Procedure,* American Petroleum Institute, RP 40, 1960. Flushing of cores by direct pressuring of solvent (flow-through) is preferred because the same apparatus can be used for oil extraction or salt leaching by using the appropriate solvents. To record the salt content in terms of mass per unit of pore volume, it is next necessary to measure the aggregate volume of the samples' void or pore spaces, i.e., pore volume, at step 24. Methods for making such a pore volume determination are described in *API Recommended Practice for Core Analysis Procedure,* API, RP 40, 1960, pg. 16–45 and *Petroleum Engineering Handbook,* Howard B. Bradley, Editor, Soc. of Petroleum Engineers, 1987, Chapter 26. Salt content is then recorded at step 12 in units of milligrams per milliliters of pore volume. It is to be noted that this is not a salinity measurement in parts per million.

Figure 3:
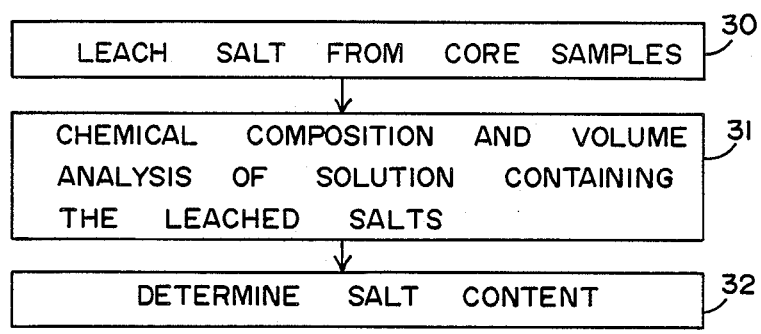

An alternate method to that shown in FIG. 2 for determining salt content is shown in FIG. 3. This method may be applied when the core samples are from reservoirs containing low salinity formation water or high oil or gas saturation (low water saturation). These samples may not yield an accurately measurable salt content by the weight difference technique described above. In such instances, and to avoid using excessively large core plugs, the salt content can be derived by other, more accurate techniques. As in the alternate method described above, the salt is leached from the dried core plugs at step 30. The solvent containing the leached salts can be analyzed at step 31 using chemical analysis, such as inductively coupled plasma atomic emission spectroscopy (ICP) and titrimetric techniques. These techniques are described in "Standard Methods for the Examination of Water and Waste Water," Am. Public Health Association, Am. Water Works Association, and Water Pollution control Federation, 16th Edition (1985), and API Recommended Practice for Analysis of Oil Field Waters, American Petroleum Institute, RP 45, 1968. (When methanol is used as the solvent, it can be replaced by distilled water by vaporizing and redissolution.) From the compositional analysis and volume of the solution, the salt content in terms of mass per unit volume can be recorded at step 32. (In certain areas where the ratio between the total dissolved solids and a particular reference element or ion species such as chloride is known, the determination of the chloride content simplifies the analysis procedure.)

Figure 4:
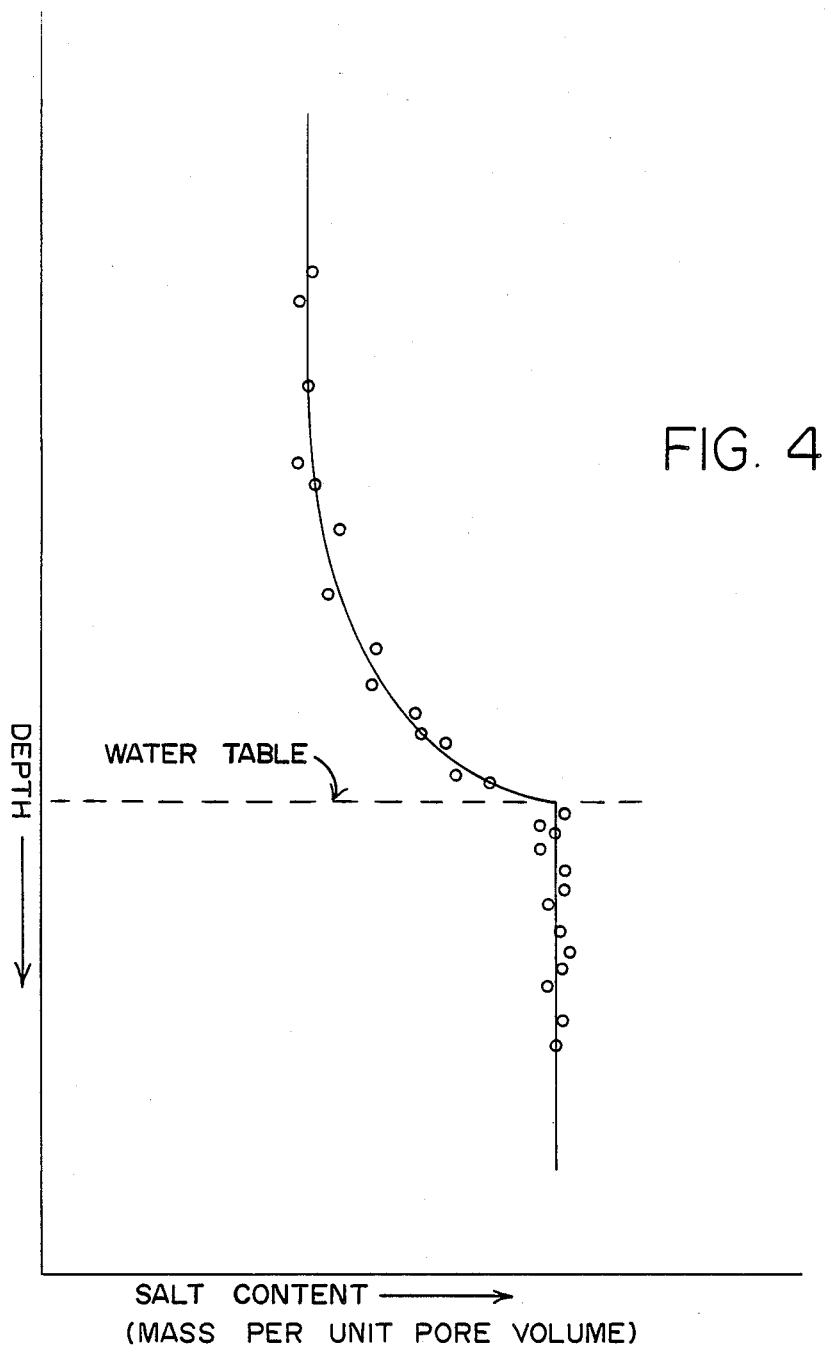
FIG. 4 is a plot depicting salt content versus depth based on measurement of salt content in core samples taken from a plurality of differing depths in a borehole traversing subterranean formations.

Referring again to FIG. 1, the salt contents of such core plugs are now correlated, such as by plotting at step 13. Such a plot is shown in FIG. 4 where it can be observed that salt content increases with depth. This is attributed to the fact that water saturation increases with depth and there is a one-to-one correspondence between water saturation and salt content. When the formation depth reaches a water table, i.e., a point of 100% water saturation, such as at a hydrocarbon-water contact, the measured salt content no longer increases.

Consequently such a correlation of salt contents of a plurality of core samples taken from differing borehole depths can be used at step 14 to identify formation characteristics. For example, a plot of salt content versus depth provides a saturation profile with formation depth. The intersection of the best fit line passing through the data points which indicate constant water saturation, with the best fit curve passing through the data points which indicate decreasing water saturation, is the hydrocarbon-water contact. The highest salt content indicated on the graph of FIG. 4 would correspond to a water saturation of 100%. Because of the linear, one-to-one relationship between water saturation and salt content, the abscissa can be converted to a water saturation scale ranging from 0–100%. Using Equation 5, the height above the water table, being zero at the water table, can be used to derive values for capillary pressure, thus resulting in a capillary pressure-saturation relationship at the in-situ state of reservoir wettability and at the in-situ reservoir conditions of pressure and temperature. Comparison of the resulting capillary pressure at one or more intermediate saturation points with laboratory-derived data on similar rock samples can result in derivation of the correct conversion factor for use in Equation 6, namely, $(\delta ow\ COS\theta)_R/(\delta ow\ COS\theta)_L$. The effect of layering or permeability variation can be revealed from the salt content data of FIG. 5 which illustrates salt content versus depth for a reservoir composed of two layers where layer 1 possesses a larger permeability than layer 2. If rock properties vary such that the water table and/or the capillary retention properties of the rocks vary with depth, the data can reveal such variations in lithology with a relatively high degree of resolution. Furthermore, correlation of the data with electric logs can yield the correct values for the saturation exponent (Equation 1) that would result in a match between log-derived saturations and salt content-data-derived saturations. Such correlations can be used in other logged, but not cored, wells.

The derived water saturation data can be easily corrected if the formation water salinity varies with depth. The correct water saturation would be obtained by multiplying the apparent saturation by the ratio of the water salinity in parts per million at a particular depth to that at or slightly below the hydrocarbon-water contact. More simply, the correct water saturation in percent is equal to the ratio of the actual salt content in mass per unit pore volume to the equivalent salt content in the same unit pore volume when it is 100% filled with brine (the latter being derived from known water salinity and specific gravity) multiplied by 100.

The method of the present invention has the advantage that coring fluid is not important, provided filtrate loss is low and further, because water evaporation losses from the difference in the high temperature and pressure conditions of the subterranean formation to ambient conditions in the laboratory are not relevant because the salt precipitates inside the core sample.

While the foregoing has described the method of the present invention for identifying formation characteristics from salt content, it is to be understood that various modifications to the disclosed method may become apparent to one skilled in the art without departing from the scope and spirit of the invention as set forth in the appended claims.

I claim:

1. A method for determining the fluid characteristics of subterranean formations, comprising the steps of:
   (a) obtaining core samples from a plurality of differing depths with said subterranean formations,
   (b) drying said plurality of core samples to effect an evaporation of the water content of said core samples,
   (c) determining the salt content of said plurality of core samples,
   (d) correlating the determined salt content of said plurality of core samples with the differing depths from which said plurality of core samples were obtained, and
   (e) determining the fluid characteristics of said subterranean formations at in-situ reservoir conditions, of pressure and temperature and at the in-situ state of reservoir wettability, from trends identified in the correlation of the salt contents of said plurality of core samples with depth.

2. The method of claim 1 wherein the step of determining salt content comprises the steps of:
   (a) measuring the weight of said dried plurality of core samples,
   (b) leaching salt from said dried plurality of core samples,
   (c) measuring the weight of said leached plurality of core samples,
   (d) determining the weight of salt leached from said core samples from the weight difference of said dried core samples and said leached core samples,
   (e) measuring the pore volume of said plurality of leached core samples, and
   (f) determining the salt content of said plurality of core samples in terms of the weight of salt leached from said core samples and the measured pore volumes of said core samples.

3. The method of claim 1 wherein the step of determining salt content comprises the steps of:
   (a) leaching salt from said dried plurality of core samples,
   (b) performing chemical compositional and volume analysis of the solution leached from said core samples, and
   (c) determining the salt content of said plurality of core samples in terms of the weight of salt leached from said core samples and the volume of said leached salt as identified from said chemical analysis.

4. The method of claim 1 further comprising the step of determining fluid saturation in said subterranean formations from an identifiable trend in said salt content correlation.

5. The method of claim 4 wherein 100% fluid saturation is determined for a formation interval over which there is no identifiable change in salt content with depth.

6. The method of claim 5 wherein the top of a 100% fluid saturated interval is identified as the water table.

7. The method of claim 5 wherein the top of a 100% fluid saturated interval is identified as the depth of a hydrocarbon-water interface.

8. The method of claim 4 wherein said determined fluid saturation provides for a capillary pressure versus saturation relationship at the in-situ reservoir conditions of pressure and temperature and at the in-situ state of reservoir wettability.

9. The method of claim 4 wherein correlation of said determined fluid saturation exponents that are used to calibrate said electric logs in uncored wells in the same reservoir to provide additional fluid saturation determinations.

10. The method of claim 1 wherein the drying of said plurality of core samples is completed after the entire water content of said core samples has evaporated, leaving behind its salt precipitate.

11. The method of claim 10 wherein said drying is completed when there is no further weight change in said core samples.

* * * * *